United States Patent [19]

Van Breen et al.

[11] 3,994,439
[45] Nov. 30, 1976

[54] SLOW-RELEASE AIR FRESHENER POLYMER-BLEND COMPOSITION

[75] Inventors: Adriaan W. Van Breen; Gerrit Nitters, both of Delft, Netherlands

[73] Assignee: Shell Oil Company, Houston, Tex.

[22] Filed: Feb. 18, 1975

[21] Appl. No.: 550,482

[30] Foreign Application Priority Data
Feb. 20, 1974  United Kingdom............... 7774/74

[52] U.S. Cl................................. 239/54; 252/522; 260/31.8 DR; 260/876 B
[51] Int. Cl.² ..................... A24F 25/00; A61L 9/04
[58] Field of Search ................ 260/876 B; 252/522; 239/54

[56] References Cited
UNITED STATES PATENTS

| | | |
|---|---|---|
| 3,567,119 | 3/1971 | Wilbert et al............................ 239/6 |
| 3,688,985 | 9/1972 | Engel.................................... 239/54 |

FOREIGN PATENTS OR APPLICATIONS

| | | |
|---|---|---|
| 1,188,922 | 4/1970 | United Kingdom |
| 599,237 | 3/1948 | United Kingdom |

*Primary Examiner*—Richard B. Turer

[57] ABSTRACT

Slow-release air freshener compositions having favorable depletion characteristics comprise an odorant (perfume) intimately dispersed in a polymeric mixture comprising 10–50% by weight of a certain block copolymer, 2–10% by weight polystyrene and 30–50% by weight of ethylene vinyl acetate copolymer.

4 Claims, No Drawings

SLOW-RELEASE AIR FRESHENER POLYMER-BLEND COMPOSITION

BACKGROUND OF THE INVENTION

The invention relates to slow-release air freshener compositions comprising a perfume intimately dispersed in a unique combination of three thermoplastic carriers in specified proportions.

It is known to incorporate an odorant in a polymer carrier such as polyvinyl chloride. Exposure of the resulting composition to the air over a prolonged period of time may result in the emission of the odorant at the surface of the composition. Compositions of this kind are designated in this application as slow-release air freshener compositions.

In order to be effective and practical as a slow-release air freshener, the composition should generally meet the following two criteria. Firstly, it should be of such quality that when allowing the odorant to evaporate into a space such as a room through the surface of the carrier, a concentration of odorant can be obtained in that space which is sufficiently high to achieve odor control in the room. Secondly, for practical and aesthetic reasons it is desirable that the composition, while meeting the first criterion, also has a reasonable high compactness, which can be achieved if the diffusivity of the odorant in the polymer carrier is relatively high.

The known composition comprising polyvinyl chloride and an odorant generally does not meet these essential requirements, but it has surprisingly been found that, if a combination of three certain thermoplastic carriers are used, a very suitable slow-release air freshener composition can be obtained.

SUMMARY OF THE INVENTION

The invention provides a slow-release air freshener composition having favorable depletion characteristics comprising from 5–35% by weight perfume intimately dispersed in a polymeric mixture of (a) from 10–50% by weight of a block copolymer having the general formula A-B--(A)$_{0-1}$, A--(B-A)$_{2-5}$ or A-B--(B-A)$_{2-5}$ wherein A is a polymer block of styrene or alpha-methyl styrene having a molecular weight of from 5,000 to 50,000 and B is a polymer block of butadiene or isoprene having a molecular weight of 40,000 to 500,000, the amount of A being in the range of 10–65% by weight of the total block copolymer; (b) from 2–10% by weight of polystyrene; and (c) from 10–66% by weight of an ethylene vinyl acetate copolymer of the formula

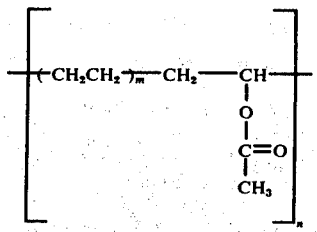

wherein $m$ is an integer from 1 to 30 and $n$ is an integer from 15 to 250.

Detailed Description of the Invention

Perfumes (fragrances) which may be employed in compositions of this invention are many and varied and it would serve little purpose to try and elucidate each and every perfume which can be utilized herein. The only essential requirements for the perfumes herein employed are that they be dispersible in the polymeric mixture and volatilizable therefrom. In general, suitable perfumes will have a boiling point in the range of about 150°–350° C, preferably 200°–300° C.

Suitable fragrances may be comprised of single chemical constituents or may be blends of many different chemical compounds which may be of natural or synthetic origin. These fragrances include alcohols, aldehydes, ethers, ketones, esters and frequently also hydrocarbons which are combined in fixed proportions so that the odor of the individual compounds will combine to produce a harmonious fragrance. In perfumery practice these compounds are combined by the blending of natural essential oils, gums, resins, animal derivatives, natural isolates and synthetic chemicals. In practice, most perfumes are blends of many types of chemicals and their composition is of a proprietary nature and hence normally designated by trade name rather than by chemical composition. Because of this, and since the efficacy of the present compositions is not dependent on the use of any particular perfume, no attempt has been made to define the perfume with the same chemical preciseness as the polymeric mixture, nor would it be possible to do so. As an example of one of many suitable perfumes is mentioned that sold by International Flavor And Fragrances (IFF), Holland under the tradename "Everfresh" which is a proprietary blend of some 20–25 different components.

As previously mentioned the block copolymers which can be suitably employed in the compositions of the invention have the general configuration A-B--(A)$_{0-1}$, A--(B-A)$_{2-5}$ or A-B--(B-A)$_{2-5}$ where A and B are as defined above. Wherever adjacent blocks are substantially identical, e.g., B-B, they are to be regarded as a single polymer block. The block polymers may be either linear or branched in their configuration and are made by processes already known in the art of polymerization such as by solution polymerization involving lithium initiators.

The following species are typical of the block copolymers contemplated, it being stressed that for the sake of simplicity in the following list only block copolymers having three blocks are mentioned.

Poly(alpha-methyl styrene)-polyisoprenepoly(alpha-methyl styrene);
Polystyrene-polyisoprene-polystyrene;
Polystyrene-polybutadiene-polystyrene.

Of the foregoing, the latter configuration e.g., polystyrene-polybutadiene-polystyrene is particularly preferred. The weight ratio of perfume (which term is also defined to include deodorants) to block copolymer preferably varies from 1:5 to 5:1.

The general formula for the ethylene vinyl acetate copolymers which are used in the compositions of the invention was hereinbefore given. It is mentioned that the actual occurrence of those acetate substituents along the hydrocarbon chain in this formula is of a random character and thus the letter $m$ in the formula denotes the average number of ethylene units per vinyl acetate unit in the molecule, rather than the presence of regularly recurrent units having the composition given within the brackets. As previously stated the value of *m* ranges from about 1 to 30, and preferably from about 2 to 17. In other words, the vinyl acetate portion of the copolymer comprises about 10–75% by weight, preferably about 15 to 50% by weight based on the total ethylene vinyl acetate copolymer.

In addition to the above-described block copolymers and ethylene vinyl acetate, the present compositions also contain from about 2–10% by weight polystyrene, a well known, commercially available polymer. Generally, the polystyrene employed in the present compositions will have an average molecular weight of at least 100,000, preferably, from 150,000 to 300,000.

Particularly attractive compositions of the invention comprise 15–25% by weight of perfume dispersed in 20–40% by weight of block copolymer as previously defined, 3–8% by weight of polystyrene and 30–50% by weight of ethylene vinyl acetate copolymer.

The compositions of the invention, which may also contain fillers, oils, dyes, anti-oxidants, stabilizers or plasticizers, may be prepared by mechanical mixing of the perfume with the polymeric carrier. The composition may subsequently be molded, extruded or otherwise formed into articles, such as strips, rods etc., which are suitable for emitting sufficient perfume into the space. The composition may be contained in a suitable holder formed from an inert material such as lacquered metal or plastic materials such as polyethylene or polypropylene, or cardboard.

The holder may be closable so that in order to achieve the desired release of odorant, the composition may be wholly or partially isolated from the atmosphere.

EXAMPLE

Four compositions (1 and 3 according to the invention; 2 and 4 for comparison) were prepared in the form of compression molded strips. The formulations and properties of each composition are summarized herebelow. The symbols A–H have the following meanings:

A — mixture of 80% polystyrene-butadienepolystyrene block copolymer (average mol. weight 14,000-64,000-14,000) and 20% naphthenic oil (Shell Flex 471);
B — polystyrene (average mol. weight 224,000);
C — ethylene vinylacetate copolymer (3:1 mixture of Dupont Elvax 150 and Elvax 260);
D — organic stabilizers (2:1 blend of Argus Mark WS and Mark C); E — pigment;
F — polyvinyl chloride (Shell Carina S-70);
G — dioctyl adipate; H — perfume (Everfresh ex IFF Holland).

| Composition | % by weight | | | |
|---|---|---|---|---|
| | 1 | 2 | 3 | 4 |
| A | 31 | — | 31 | — |
| B | 5 | — | 5 | — |
| C | 41 | — | 41 | — |
| D | 2 | 3 | 2 | 3 |
| E | 1 | 1 | 1 | 1 |
| F | — | 56 | — | 56 |
| G | — | 20 | — | 0 |
| H | 20 | 20 | 20 | 20 |
| Total weight (g) | 30 | 30 | 48 | 48 |
| Thickness (mm) | 5.0 | 5.0 | 8.0 | 4.8 |
| Emission surface area[1] volume ratio (cm²/mm) | 4.0 | 4.0 | 2.5 | 4.2 |

[1] Defined as twice the length × width of the strip

The strips were exposed to an atmosphere of 23° C/50% R.H. (relative humidity) in 16m³ rooms. The performances of the compositions are summarized herebelow.

| Room Exposure | Degree of depletion (% wt. of perfume) | | | |
|---|---|---|---|---|
| | 1 | 2 | 3 | 4 |
| 5 days | 31.7 | 18.8 | 19.7 | 19.6 |
| 10 days | 44.8 | 26.7 | 27.8 | 27.7 |
| 20 days | 62.8 | 37.7 | 39.6 | 39.3 |
| 30 days | 74.8 | 46.2 | 48.5 | 48.1 |
| 40 days | 83.0 | 53.2 | 55.8 | 55.4 |
| 50 days | 88.5 | 59.3 | 62.2 | 61.7 |
| 60 days | 92.2 | 64.5 | 67.5 | 67.0 |

From the above data it appears that at identical weight, thickness, perfume content and surface area/volume ratio composition 1 has a markedly better depletion level than composition 2 at any stage of the exposure. Consequently, when mounted in a regulatable holder, the release rate of composition 1 can be adjusted over a much wider range than is possible with composition 2. Furthermore, it appears that, at more or less identical performance, composition 3 is much more compact than composition 4. Compactness is a distinct advantage in designing air freshener compositions of attractive appearance.

What is claimed is:

1. A slow-release air freshener composition comparing from 5–35% by weight perfume intimately dispersed in a polymeric mixture of
   a. from 10–50% by weight of a block copolymer having a general formula selected from the group consisting of A-B-(-A)$_{0-1}$, A-(-B-A)$_{2-5}$ or A-B-(-B-A)$_{2-5}$ wherein A is a polymer block of styrene or alpha-methyl styrene having a molecular weight of from 5,000 to 50,000, and B is a polymer block of butadiene or isoprene having a molecular weight of 40,000 to 500,000, the amount of A being in the range of 10–65% by weight of the total block copolymer;
   b. from 2–10%w. of polystyrene; and
   c. from 10–66% by weight of an ethylene vinyl acetate copolymer of the formula

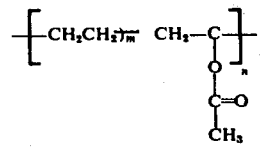

wherein *m* is an integer from 1 to 30 and *n* is an integer from 15 to 250.

2. The composition of claim 1 wherein the block copolymer has the configuration polystyrene-polybutadiene-polystyrene.

3. The composition of claim 2 wherein the perfume content is 15–25% by weight.

4. The composition of claim 3 wherein the polymeric mixture contains 20–40% by weight of block copolymer, 3–8% by weight of polystyrene and 30–50% by weight of ethylene vinyl acetate copolymer.

* * * * *